United States Patent
Boulton et al.

(10) Patent No.: US 10,543,179 B2
(45) Date of Patent: Jan. 28, 2020

(54) DOSAGE REGIMEN OF AN S1P RECEPTOR MODULATOR

(71) Applicant: Novartis AG, Basel (CH)

(72) Inventors: Craig Boulton, Horsham (GB); Pascale Burtin, Huningue (FR); Olivier David, Mulhouse (FR); Ana de Vera, Basel (CH); Thomas Dumortier, Basel (CH); Irene Hunt, Basel (CH); Robert Schmouder, Berkeley Heights, NJ (US); William C. Collins, Basel (CH)

(*) Notice: Subject to any disclaimer, the term of this patent is extended or adjusted under 35 U.S.C. 154(b) by 0 days.

(21) Appl. No.: 15/986,992

(22) Filed: May 23, 2018

(65) Prior Publication Data

US 2018/0263929 A1    Sep. 20, 2018

Related U.S. Application Data

(63) Continuation of application No. 15/646,583, filed on Jul. 11, 2017, now abandoned, which is a continuation of application No. 15/152,894, filed on May 12, 2016, now abandoned, which is a continuation of application No. 14/176,504, filed on Feb. 10, 2014, now abandoned, which is a continuation of application No. 13/497,349, filed as application No. PCT/US2010/049441 on Sep. 20, 2010, now abandoned.

(60) Provisional application No. 61/246,706, filed on Sep. 29, 2009, provisional application No. 61/258,329, filed on Nov. 5, 2009, provisional application No. 61/307,992, filed on Feb. 25, 2010, provisional application No. 61/352,029, filed on Jun. 7, 2010.

(51) Int. Cl.

| | |
|---|---|
| A61K 49/00 | (2006.01) |
| A61K 31/135 | (2006.01) |
| A61K 31/137 | (2006.01) |
| G06F 19/00 | (2018.01) |
| A61K 31/138 | (2006.01) |
| A61K 31/661 | (2006.01) |
| A61K 45/06 | (2006.01) |
| A61B 5/021 | (2006.01) |
| A61B 5/024 | (2006.01) |
| A61B 5/0402 | (2006.01) |
| A61B 5/00 | (2006.01) |
| G01N 33/487 | (2006.01) |
| G16H 50/20 | (2018.01) |
| G16H 50/30 | (2018.01) |

(52) U.S. Cl.
CPC ............ *A61K 31/135* (2013.01); *A61B 5/021* (2013.01); *A61B 5/024* (2013.01); *A61B 5/0402* (2013.01); *A61B 5/444* (2013.01); *A61B 5/4833* (2013.01); *A61K 31/137* (2013.01); *A61K 31/138* (2013.01); *A61K 31/661* (2013.01); *A61K 45/06* (2013.01); *G01N 33/487* (2013.01); *G06F 19/326* (2013.01); *G16H 50/20* (2018.01); *G16H 50/30* (2018.01)

(58) Field of Classification Search
None
See application file for complete search history.

(56) References Cited

FOREIGN PATENT DOCUMENTS

| EP | 1905434 A1 | 4/2008 |
|---|---|---|
| EP | 1923058 | 5/2008 |
| WO | WO03097028 | 11/2003 |
| WO | WO2005/025553 A2 | 3/2005 |
| WO | WO2006/058316 A1 | 6/2006 |
| WO | WO2009155475 A1 | 12/2009 |
| WO | WO2010075239 A1 | 7/2010 |

OTHER PUBLICATIONS

Maritime. Medical News Today [online]; 2006; downloaded from < URL http://www.medicalnewstoday.com/printerfriendlynews.php?newsid=53054 > on Nov. 11, 2018; 6 pages. (Year: 2006).*
Garber. Nature Biotechnology. 2008; 26(8): 844-845. (Year: 2008).*
Dowell, Scott F., and Joseph S. Bresee. "Severe varicella associated with steroid use." Pediatrics 92.2 (1993): 223-228.
Johnson "Etiology and Treatment of Macular Edema" American Journal of Ophthalmology, 2009;147:11-21.
Saab et al., "Reversible Cystoid Macular Edema Secondary to Fingolimod in a Renal Transplant Recipient", Arch Ophthalmol/vol. 126(No. 1) Jan. 2008.
Zuvich et al, "Genetics and Pathogenesis of Multiple Sclerosis", National Institutes of Health, Author Manuscript, 21(6), 328-333 (2009).
Multiple Sclerosis, Poster Presentations, 2008, vol. 14, p. S177.
Budde et al., "First Human Trial of FTY720, a Novel Immunomodulator, in Stable Renal Transplant Patients", Journal of the American Society of Nephrology, 2002, vol. 13, No. 4, pp. 1073-1083.
Koyrakh et al., "The Heart Rate Decrease Caused by Acute FTY720 Administration Is Mediated by theG Protein-Gated Potassium Channel IKACh", American Journal of Transplantation, American Society of Transplantations, 2005, vol. 5, No. 3, pp. 529-536.
Comi G. et al., "Phase II study of oral fingolimod (FTY720) in multiple sclerosis: 3-year resuPaylts.", Mult.Scler. Feb. 2010; 16(2): 197-207. [Epub Dec. 22, 2009 Abstract [on-line] [found on Sep. 10, 2014] (found in the Internet at: www.ncbi.nlm.nih.gov/pubmed/20028707)].
Kharkevich Pharmacology, M., Medicine, 1996, pp. 41 to 42 §6.A (English Translation ).

(Continued)

*Primary Examiner* — David Browe
(74) *Attorney, Agent, or Firm* — Baker Donelson

(57) ABSTRACT

The present invention relates to a dosage regimen of an S1P receptor modulator or agonist in the course of the treatment of patients suffering from an inflammatory or autoimmune disorder, for example multiple sclerosis. Specifically, the present invention relates to testing a patient for a history of infection and vaccinating the patient prior to administration of fingolimod or a pharmaceutically acceptable salt thereof at a daily dosage of 0.5 mg.

4 Claims, No Drawings

(56) References Cited

OTHER PUBLICATIONS

Belikov, "Pharmaceutical Chemistry", High School, 1993, v. 1, pp. 43 to 47, chapter 2.2 ( English Translation).
O'Connor P. et al., "Oral fingolimod (FTY720) in multiple sclerosis: two-year results of a phase II extension study", Neurology, Jan. 6, 2009;72(I):73-9. [Abstract [on-line] [found on Sep. 10, 2014] (found in the Internet at: www.ncbi.nlm.nih.gov/pubmed/ 19122034)].
Manual of Antitumor Medicaments under editorship of N.I. Perevodchikova, M., Medicine, 1993, p. 193, paragraph 2 and 3, p. 201, (English translation).
Mehling M, et al.,"FTY720 therapy exerts differential effects on T cell subsets in multiple sclerosis"; Neurology, ;vol. 71 (16): pp. 1261-1267, Oct. 14, 2008.
Robert Schmouder et al, "FTY720: Placebo-Controlled Study of the Effect on Cardiac Rate and Rhythm in Healthy Subjects" Journal of Clinical Pharmacology, vol. 46, pp. 895-904, 2006.
This Is MS, FTY720 Update, Drug Pipeline Forum, Apr. 30, 2009, http://www.thisisms.com/forum/drug-pipeline-f13/topic7150. html#p56497.
Salvadori M et al., "FTY720 versus MMF with Cyclosporine in de novo Renal Transplantation: A 1-Year, Randomized Controlled Trial in Europe and Australasia", American Journal of Transplantation, 2006, vol. 6, pp. 2912-2921.
Payne S. et al, "The immunosuppressant drug FTY720 inhibits cytosolic phospholipase A2 independently of sphingosine-1-phosphate receptors", Blood, Feb. 1, 2007, vol. 109, No. 3, pp. 1077-1085.
Kovarik J. et al, "The effect on heart rate of combining single-dose fingolimod with steady-state atenolol or diltiazem in healthy subjects", European Journal of Clinical Pharmacology, 2008, vol. 64, pp. 457-463.
Anonymous. 2008. Fingolimod FTY720 for relapsing-remitting and primary progressive multiple sclerosis. Horizon Scanning Center [online]; downloaded from U RL <http://www.hsc.nihr.ac.uk!lopics/ fly-720-fingolimod-for-multiple- Dsclerosis-relapsin/> on Aug. 29, 2013; 6 pages.
Kappas Lelal. 2006. Fingolimod (FTY720). N Eng I J Med.; 355:1124-1140.
Anonymous: "National Multiple Sclerosis Society: News Detail". Dec. 12, 2008. pp. 1-2. retrieved from the internet: URL:http:llwww. nationalmssociety.org/researchlresearch-news/news-delaillindex. aspx?nid=557.
Cohen Jeffrey A.. et al., Oral Fingolimod (FTY720) Versus Interferon Beta-1a in Results from a Phase III Study (Transforms), Neurology, ol 72, No. 11, suppl. 3, Mar. 2009, p. A254.
Kappes L. et al., "Oral Fingolimod (FTY720) for Relapsing Multiple Sclerosis", New England Journal of Medicine, Massachusetts Medical Society, Boston, MA, US, vol. 355, No. 11, Sep. 14, 2006, pp. 1124-1140, p. 1132-1138, paragraph entitled "Adverse Events".
Hutchison S., et al., "An investigation of the impact of the location and timing of antigen-specific T cell division on airways inflammation", clinical and Experimental Immunology, vol. 155, No. 1, Jan. 2009, pp. 113-114.
Spiegel S. et al., "The immunosuppressant frug FTY720 inhibits cytosolic hospholiphase A2 independently of sphingosine-1-phosphate receptors", Journal of Allergy and Clinical Immunology val. 119, No. 1, Suppl. 1, Jan. 2007, p. S313.
Cohen Jeffrey A., et al., Oral Fingolimod or intramuscular interferon for relapsing multiple sclerosis., The New England Journal of Medicine Feb. 4, 2010, vol. 362, No. 5, pp. 402-415.
Slade Alan et al., "Effects of Oral Fingolimod (FTY720) on ulmonary Function Tests in Patients with Moderate Asthma" Neurology, val. 74, No. 9, Suppl. 2, Mar. 2010, pp. A63-A64.
Dowell et al., "Severe Varicella Associated with Steroid Use", Pediatrics, 1993, vol. 92, pp. 223-228.
Nicholas et al., "Development of oral immunomodulatory agents in the management of multiple sclerosis", Drug Design, Development and Therapy, 2011, vol. 5, pp. 255-274.
Kappos et al., "A Placebo-Controlled Trial of Oral Fingolimod in Relapsing Multiple Sclerosis", New England Journal of Medicine, 2010, vol. 362, No. 5, pp. 387-401.
Ricklin et al., "T-cell response against varicella-zoster virus in fingolimod-treated MS patients", Neurology, 2013, vol. 81, pp. 174-181.
Calabresi et al., "Safety and efficacy of fingolimod in patients with relapsing-remitting multiple sclerosis (Freedoms II): a double-blind, randomized, placebo-controlled, phase 3 trial", The Lancet Neurology, 2014, vol. 13, pp. 545-556.
Arvin et al., "Varicella-Zoster Virus Infections in Patients Treated with Fingolimod", JAMA Neurology, 2015, vol. 72, No. 1, pp. 31-39.
Tyler, "Fingolimod and Risk of Varicella-Zoster Virus Infection", JAMA Neurology, 2015, vol. 72, No. 1, pp. 10-13.
Ratchford et al., "Varicella-Zoster Virus Encephalitis and Vasculopathy in a Patient Treated with Fingolimod", Neurology, 2012, vol. 79. pp. 2002-2004.
Gross et al., "Multiple Sclerosis Rebound Following Herpes Zoster Infection and Suspension of Fingolimod", Neurology, 2012, vol. 79, pp. 2006-2007.
Issa et al., VZV Encephalitis that Developed in an Immunized Patient During Fingolimod Therapy», Neurology, 2015, vol. 84, pp. 99-100.
Winkelmann et al., "Fingolimod Treatment for Multiple Sclerosis Patients What Do We Do with Varicella?", Annals of Neurology, 2011, vol. 70, No. 4, pp. 673-674.
Cohen J S: Ways to minimize adverse drug reactions. Individualized doses and common sense are key., Postgraduate Medicine Sep. 1999, vol. 106, No. 3, Sep. 1999( Sep. 1999), p. 163, XP9174475;.
Schmouder, R. et al., 'Oral fingolimod (FTY720), 0.5 or 1.25 mg, for 14 days has no effect on cardiac function', Multiple Sclerosis, Sep. 17, 2008, vol. 14, pp. S29-S293, (See S177, P507).
Caballero, S. et al., 'Anti-sphingosine-1-phosphate monoclonal antibodies inhibit angiogenesis and sub-retinal fibrosis in a murine model of laser-induced choroidal neovascularization', Experimental Eye Research, Mar. 2009, vol. 88, No. 3 pp. 367-377.
Romine et al., "A double-blind, placebo-controlled, randomized trial of cladribine in relapsing-remitting multiple sclerosis", Proc Assoc Am Physicians, Jan.-Feb. 1999;111(1):35-44 (Abstract); Downloaded from PubMed.gov at https://www.ncbi.nlm.nih.gov/pubmed/ 9893155.
Cohen, Jeffrey I., "Strategies for Zoster Vaccination in Immunocompromised Patients", J Infect Dis. Mar. 1, 2008; 197 (Suppl 2): S237-S241 ; Downloaded from https://www.ncbi.nlm. nih.gov/pmc/articles/PMC2679676/.
*Clinical Development, FTY720(fingolimod), NDA 22-527, Erratum to briefing Document for FDA Advisory Committee Meeting, Jun. 10, 2010.
*Fingolimod (NDA 22-527), Briefing document, Prepared by Novartis Pharmaceuticals for the Peripheral and Central Nervous Systems Drugs Advisory Committee Meeting, pp. 1-112, Jun. 10, 2010.
*FDA/CDER, Peripheral and central Nervous System Drugs Advisory Committeee Meeting, Fingolimod, (NDA 22-257) Background Package, Jun. 10, 2010.
*Errata—FDA Briefing Document for NDA 22-527 (fingolimod) Peripheral and Central Nervous System Drugs Advisory Committee Meeting Jun. 10, 2010.
*Memorandum, Department of Health & Human Services, Public Health Service, Food and Drug Administration, Subject: NDA 22,527 for fingolimod, Jun. 1, 2010.
*Federal Drug Administration Center for Drug Evaluation and Research Peripheral and Central Nervous system Drugs Advisory Committee Meeting Jun. 10, 2018, Transcript.
*Gershon et al., "Advances in the understanding of the pathogenesis and epidemiology of herpes zoster", Journal of Clinical Virology, vol. 48, S1, S2-S7, (2010).
*Tedesco-Silva et al., "Randomized Controlled Trial of FTY720 Versus MMF in De Novo Renal Transplantation", Transplantation, vol. 82, No. 12, Dec. 27, 2006.
*Kappos et al., "Safety findings from a 12-month phase III study (Transforms) comparing oral fingolimod (FTY720) and intramus-

(56) References Cited

OTHER PUBLICATIONS cular interferon b-1a for relapsing-remitting multiple sclerosis", P807, Multiple Sclerosis, vol. 15, S245-246, (2009).
*Makri et al., Drug-Induced Macular Edema,Drugs, Vo. 73, pp. 789-802, (2013).
*Gelfand et al., "Microcystic macular oedema in multiple sclerosis is associated with disease severity", Brai, vol. 135, pp. 1786-1793, (2012).
*Fraunfelder et al., "Adverse ocular effects associated with niacin therapy" British Journal of Ophthalmology, vol. 79, pp. 54-56, (1995).
*Jain and Bhatti, "Fingolimod-associated macular edema—Incidence, detection, and management", Neurology, vol. 78, pp. 672-680, (2012).
VARIVAX—Summary of Product Characteristics; Dec. 19, 2013; Sanofi Pasteur MSD Limited.
VARILRIX—Summary of Product Characteristics; Apr. 20, 2015; GlaxoSmithKline UK.
"Harrison's principles of internal medicine" (15th edition, 2001).
Dixon, W. G., et al. "Serious infection following anti-tumor necrosis factor αtherapy in patents with rheumatoid arthritis: lessons from interpreting data from observational studies." Arthritis & Rheumatism: Official Journal of the American College of Rheumatology 56.9 (2007): 2896-2904.
Okhravi et al. Octal Immunol Inflamm. 2003; 11(1): abstract. (Year: 2003).
Berger, Joseph R., et al. "Considerations on discontinuing natalizumab for the treatment of multiple sclerosis." Annals of neurology 68.3 (2010): 409-411.
ICH Harmonised Tripartite Guideline; Clinical Safety Data Management: Definitions and Standard for Expedited Reporting E2A; Oct. 27, 1994.
Stedman, Thomas Lathrop. "Stedman's Medical Dictionary" (27th edition, 2000).
Lemtrada U.S. label dated Dec. 2017.
Mavenclad U.S. label dated Mar. 2019.
Mayzent U.S. label dated Mar. 2019.
Mulero, Patricia, et al. "Varicella-zoster meningovasculitis in a multiple sclerosis patient treated with natalizumab." Multiple Sclerosis Journal 24.3 (2018): 358-360.
Nightingale, Stuart L. "From the food and drug administration." Jama 267.3 (1992): 339.
Ontaneda, Daniel, et al. "Early tolerability and safety of fingolimod in clinical practice." Journal of the neurological sciences 323.1-2 (2012): 167-172.

* cited by examiner

DOSAGE REGIMEN OF AN S1P RECEPTOR MODULATOR

The present invention relates to a dosage regimen of an S1P receptor modulator or agonist in the course of the treatment of patients suffering from an inflammatory or autoimmune disease or disorder, for example multiple sclerosis (MS).

Multiple sclerosis is the chief cause of neurological disability in young adults and the most common demyelinating disorder of the central nervous system. Available therapies such as interferon-β and glatiramer acetate have modest efficacy and marginal effects on the progression of disability. These biological agents are administered parenterally and are associated, e.g., with injection site reactions and pyretic symptoms, such as flu-like symptoms. Therefore, there is a strong medical need for a safe and effective oral treatment of multiple sclerosis.

Of those people with multiple sclerosis who receive treatment, a significant number continue to experience disease activity clinically or experience side effects that include flu-like symptoms. Immediate post-injection reactions and injection site reactions. As a result, a substantial population of patients are untreated. Including many with active disease. These MS patients have either tried an existing therapy but discontinued due to intolerance, adverse effects, or perceived lack of efficacy or have not started any therapy because of their concern with adverse effects, fear of self-injection, fear of needles, or belief that currently available options are not effective enough to warrant trial. Thus, there is a significant unmet need for effective new therapies in MS, which limit or reduce the possible adverse events or side effects.

S1P receptor modulators are compounds which signal as agonists at one or more sphingosine1-phosphate receptors, e.g. S1P1 to S1P5. Agonist binding to a S1P receptor may e.g. result in dissociation of intracellular heterotrimeric G-proteins into Gα-GTP and Gβγ-GTP, and/or increased phosphorylation of the agonist-occupied receptor and activation of downstream signaling pathway kinases.

S1P receptor modulators are valuable compounds for the manufacture of medication for the treatment of various conditions in mammals, especially in human beings. For example, efficacy in transplantation has been demonstrated in rats (skin, heart, liver, small bowel), dogs (kidney), and monkeys (kidney) models. Due to their immune-modulating potency, S1P receptor modulators are also useful for the treatment of inflammatory and autoimmune diseases. Treating such diseases usually requires prolonged taking of medication, and maintaining the adequate drug regimen over time.

Oral fingolimod is the first compound in the new class of therapeutics called sphingosine 1-phosphate receptor modulators. Fingolimod is believed to reduce the number of lymphocytes circulating in the blood stream by reversibly trapping a proportion of them in the lymph nodes. Consequently, the number of activated lymphocytes reaching the brain is decreased, resulting in reduced inflammatory destruction. This is a new mechanism of action for MS.

FTY720 efficacy in the treatment of multiple sclerosis has been shown in humans (e.g. as described in "FTY720 therapy exerts differential effects on T call subsets in multiple sclerosis". Mehling M, et al., Neurology. 2008 Oct. 14; 71(16):1281-7; and "Oral fingolimod (FTY720) for relapsing multiple slerosls". Kappos L, Antel J, Comi G, Montalban X, O'Connor P, Polman C H, Haas T, Korn A A, Karlsson G, Radue E W; FTY720 D2201 Study Group. N Engl J Med. 2006 Sep. 14; 355(11):1124-40.).

Administration of a S1P receptor modulator, such as fingolimod may induce adverse events, such as a transient reduction of the heart rate and cardiac conduction at treatment initiation. In particular it has been described that administration of 1.25 mg of FTY720 may induce a decrease in heart rate of approximately 8 beets/min ("FTY720: Placebo-Controlled Study of the Effect on Cardiac Rate and Rhythm in Healthy Patients", Robert Schmouder, Denise Serra, Yibin Wang, John M. Kovarik, John DiMarco, Thomas L. Hunt and Marie-Claude Bastien. J. Clin. Pharmacol. 2006; 46; 895.).

Because of such a possible adverse event, administration of the compound to the patients may have to be made under full and constant medical control, in order to check that the cardiac rhythm is maintained at an acceptable level and no high degree atrioventricular block occurs. Patients may have to stay in hospitals which complicate the treatment and increase the costs of treatment occurrence of adverse events during a drug treatment may induce patient hospitalization or prolongation of existing hospitalization.

Such possible events may also cause the patients to interrupt their treatment, change the recommended dosing regimen on their own or take the medication on an irregular basis, without any medical support or recommendation for doing that. While it is paramount for treating inflammatory or autoimmune diseases, such as for example multiple sclerosis, that the adequate medication is taken over a long period of time, sometimes during the whole life of the patient, and the adequate drug regimen is kept over such a long period of time.

Therefore there is a need to reduce or manage the possible adverse events which may be generated by administration of such a S1P receptor modulator, while administering a dosage which is adequate to treat or prevent the disease for which the compound is administered during the required period of treatment.

More specifically, there is a need to provide an efficient treatment for treating an inflammatory or autoimmune disease or disorder, such as multiple sclerosis, for a large population of multiple sclerosis patients, including patients who could be more exposed or more sensitive to said possible adverse events, patients who were never treated or diagnosed for an inflammatory or autoimmune disease or disorder There is furthermore a need to ameliorate patient compliance.

BRIEF DISCLOSURE OF THE INVENTION

Surprisingly it has been found that by administering a S1P receptor modulator or agonist, such as fingolimod, according to the specific dosage regimen or method of treatment of the invention, it is possible to treat the patient efficiently while controlling, reducing or abolishing the possible adverse events, e.g. side effects, which may be associated with administration of such a compound.

A further benefit is that the dosing regimen and methods of treatment of the invention permit to administer a S1P receptor modulator or agonist, such as fingolimod, to patients who otherwise may have been reluctant or not could not have been instructed to take that medication. In particular they permit to treat patients suffering from an inflammatory or autoimmune disease or disorder, such as multiple sclerosis, for which the ratio risk/benefit may otherwise be less favourable. Such patients are for example patients susceptible to or suffering from one or more disease or disorders affecting the heart or heart rhythm, respiratory functions, eyes, hepatic functions. This also concerns patients that have undergone an interruption or treatment holiday in the maintenance dosage regime e.g. a holiday of greater than 10 days.

Furthermore the dosing regimen and methods of treatment of the invention is applicable for patients who were already under treatment for an inflammatory or autoimmune or disease, for example under treatment for multiple sclerosis, as well as patients who were never treated or were not diagnosed for an inflammatory or autoimmune or disease before taking a S1P receptor modulator or agonist.

The dosage regimen of the present invention is a regimen for a S1P receptor modulator or agonist therapy, which enables administration of a therapeutic dosage range of the S1P receptor to be achieved with controlled or minimal side effects, which could otherwise have been possibly associated with S1P receptor modulator therapy.

Another benefit of the present invention is to provide an therapeutic regimen for an inflammatory or autoimmune or disease, such as multiple sclerosis, which can be personalized, e.g. adapted to the specific profile of the patient to be treated and/or to the state of the disease in this patient, in such as way that that the disease is treated (or the disease severity is reduced), while the adverse events which could otherwise have been associated with administering said S1P receptor modulator or agonist are controlled, reduced, or abolished. For example, therapeutic regimen of the present invention may be personalized in view of the other diseases or disorders the patient could be affected with, the other medication he could be taken, e.g. depending of whether he is suffering from a heart disease or disorder.

S1P Receptor Modulators or Agonists

According to the invention, specific S1P receptor modulators of the invention are 2-amino-2-tetradecyl-1,3-propanediol. An example of S1P receptor modulator is fingolimod (FTY720), i.e. 2-amino-2-[2-(4-octylphenyl) ethyl] propane-1,3-diol in free form or in a pharmaceutically acceptable salt form, e.g. the hydrochloride, as shown:

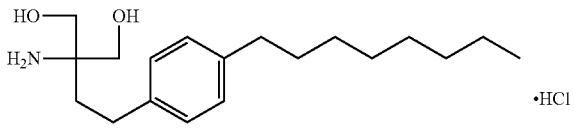 [SMILES: CCCCCCCCc1ccc(CCC(N)(CO)CO)cc1 ; Cl]

Another specific S1P receptor modulator of the invention is the phosphorylated derivative of FTY720, also referred to as fingolimod-phosphate, as shown:

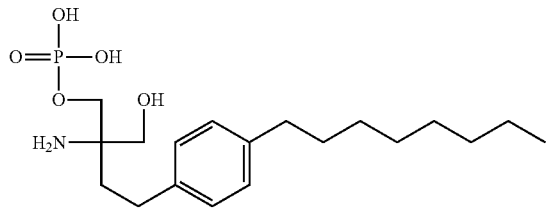 [SMILES: CCCCCCCCc1ccc(CCC(N)(CO)COP(=O)(O)O)cc1]

Preferably, the S1P receptor modulator or agonist of the invention, e.g. fingolimod in free form, in a pharmaceutically acceptable salt form or fingolimod-phosphate, is administered orally.

Dosage Regimen

As previously stated, the present invention provides a new dosage regimen and method for treating an inflammatory or autoimmune disease or disorder in a patient in need thereof, comprising administering to said patient a S1P receptor modulator or agonist, such as fingolimod (FTY720), a phosphate derivative thereof or a pharmaceutically acceptable salt thereof, in such a way that the disease is treated or the disease severity is reduced, while the adverse events possibly associated with administration of said S1P receptor modulator or agonist are controlled, limited, reduced or abolished. For example there is provided a method for treating an inflammatory or autoimmune disease or disorder in a patient in need thereof, comprising administering to said patient a S1P receptor modulator or agonist, such fingolimod (FTY720), a phosphate derivative thereof or a pharmaceutically acceptable salt thereof, in such as way that the symptoms of the disease are reduced or abolished while the adverse events possibly associated with administration of said S1P receptor modulator or agonist are controlled, limited, reduced or abolished.

According to the invention there is provided a method for administering FTY720, a phosphate derivative thereof or a pharmaceutically acceptable salt thereof, to a patient in need thereof preferably refers to a method for treating an inflammatory or autoimmune disease or disorder, limiting the symptoms associated thereof or the progression thereof, e.g. multiple sclerosis, in a patient in need thereof. In particular it refers to a method for treating RRMS, limiting the symptoms associated thereof or the progression thereof in a patient in need thereof.

According to the present invention the terms "treatment" or "treat" refer to both prophylactic or preventive treatment as well as curative or disease-modifying treatment, including treatment of patients at risk of contracting the disease or disorder, or suspected to have contracted the disease or disorder, as well as patients who are ill or have been diagnosed as suffering from the disease or disorder.

Autoimmune diseases or disorders according to the invention are preferably chronic long term diseases, e.g. multiple sclerosis (MS), for example relapsing remitting multiple sclerosis (RRMS) or primary progressive multiple sclerosis (PPMS), e.g. RRMS. MS takes several forms, with new symptoms occurring either in discrete attacks (relapsing forms) or slowly accumulating over time (progressive forms).

The dosing regimens and methods of treatment according to the present invention are particularly adapted for multiple sclerosis, e.g. RRMS.

As herein defined, treating multiple sclerosis refers to, but is not limited to, reducing the frequency of clinical exacerbations or delaying the accumulation of physical disability induced by multiple sclerosis. It may also refer to limiting the symptoms of the disease.

As herein defined, symptoms or disorders associated with multiple sclerosis encompass neurological symptoms, physical and cognitive disability and neuropsychiatric disorders.

As herein defined, adverse event refers to any adverse change in health that occurs to a patient receiving a treatment or within a specified period of time after the treatment has been completed. Controlling the adverse events refers to limiting the extension, outcome, consequences or impact of such events in such a way that the patient's health is not a risk, or the treatment can be continued without worsening the overall health of the patient. The adverse events are not necessarily related to the medication itself, they may also be related to the inflammatory or autoimmune disease or disorder for which the patient is treated or another disease or disorder that the patient is further affected with.

According to the invention reduction of the adverse events refers to the reduction of the events, e.g. of side-effects, to a level that is acceptable to the patient safety, e.g. which does not require specific treatment and/or specific medical care, hospitalization or medical monitoring. For example reduction of the adverse events refers to the reduction of the events to a level that is acceptable for the patient compliance.

According to the invention limitation of the adverse events refers to limitation of the number or occurrence of adverse events, e.g. of side-effects, in a patient, to a number or occurrence which is acceptable to the patient, e.g. which does not require specific treatment and/or specific medical care, hospitalization or medical monitoring. For example limitation of the adverse events refers to limitation of the number or occurrence of adverse events to a number or occurrence that is acceptable for the patient safety end/or compliance.

The monitoring of possible adverse events may be done as described herein above. For example it may be done by ophthalmic examination, dermatologic examination, pulmonary function tests, chest X-ray and/or CT, Holter monitoring, and/or echocardiography. In a specific embodiment of the invention, the monitoring and reporting of adverse events comprises the monitoring and reporting of bradycardia, syncope or pre-syncope, serious infectious, liver toxicity, and macular edema.

As herein defined, a patient treated with fingolimod (FTY720) refers to a patient receiving fingolimod (FTY720), a phosphate derivative thereof (i.e. fingolimod-phosphate) or a pharmaceutically acceptable salt thereof, for treating an inflammatory or autoimmune disease or disorder according to the invention, e.g. MS, e.g. RRMS.

As herein defined, a patient in need of prescribing fingolimod refers to a patient suffering from an inflammatory or autoimmune disease or disorder according to the invention, e.g. a MS patient.

Patients treated with fingolimod (FTY720) and the patients in need of prescribing fingolimod may be patients who have never received treatment for an inflammatory or autoimmune disease or disorder, such as patients who have never received a treatment for treating or preventing MS, as well as patients who previously received one or more treatment for an inflammatory or autoimmune disease or disorder, for example who previously received one or more treatment for MS.

The effectiveness of the S1P modulator of the invention in treating multiple sclerosis may be evaluated by medical standards and criteria known to the skilled person. For example, it can be evaluated through annual relapse rate of multiple sclerosis.

For example, the dosage of the S1P receptor modulator or agonist of the invention can be considered as efficient for treating the disease or reducing the symptoms associated thereof, e.g. for treating multiple sclerosis, when the relapse rate is decreased by more than 45%, e.g. more than 50%, e.g. more than 80%.

In another embodiment effectiveness of the S1P receptor modulator or agonist of the invention in treating multiple sclerosis is evaluated through the disability progression, e.g. according to the Kurtzke Expanded Disability Status Scale (EDSS). The Kurtzke Expanded Disability Status Scale (EDSS) is a method of quantifying disability in multiple sclerosis. The EDSS quantifies disability in eight Functional Systems (FS) and allows neurologists to assign a Functional System Score (FSS) in each of these. For example, the dosage of the S1P receptor modulator or agonist of the invention can be considered as efficient for treating the disease or reducing the symptoms associated thereof, e.g. for treating multiple sclerosis, when progression of the patient disability is delayed by at least 25%, e.g. by at least 30%, e.g. by at leapt 32%.

The effectiveness of the dosing regimen of the invention may also be evaluated by measuring brain lesions. e.g. by Magnetic Resonance Imaging (RMI) scans.

Monitoring

The present invention provides a dosing regimen and a method for treating an inflammatory or autoimmune disease or disorder in a patient in need thereof, comprising administering to said patient a therapeutically effective amount of a S1P receptor modulator or agonist, wherein said method comprises the steps of
  i) monitoring the patient during a specific period of time after the first administration of said S1P receptor modulator or agonist, and
  ii) optionally interrupting the administration of said S1P receptor modulator or agonist and/or modifying the treatment regimen thereof and/or administering a second drug which mitigates said possible adverse events.

Such a dosing regimen is particularly adapted for administering fingolimod, e.g. in patient suffering from multiple sclerosis.

Furthermore there is provided a S1P receptor modulator or agonist, e.g. FTY720, a phosphate derivative thereof or a pharmaceutically acceptable salt thereof, for use in the treatment of an inflammatory or an autoimmune disease or disorder, e.g. multiple sclerosis, wherein said treatment comprises the steps of
  i) monitoring the patient during a specific period of time after the first administration of said S1P receptor modulator or agonist, and
  ii) optionally interrupting the administration of said S1P receptor modulator or agonist and/or modifying the treatment regimen thereof and/or administering a second drug which mitigates said possible adverse events.

In a specific embodiment, the present invention provides FTY720, a phosphate derivative thereof or a pharmaceutically acceptable salt thereof, e.g. the hydrocloride salt of FTY720, for use in the treatment of multiple sclerosis, wherein said treatment comprises the steps of
  i) monitoring the patient during a specific period of time after the first administration of FTY720, a phosphate derivative thereof or a pharmaceutically acceptable salt thereof, and
  ii) optionally interrupting the administration of FTY720, a phosphate derivative thereof or a pharmaceutically acceptable salt thereof, and/or modifying the treatment regimen thereof, and/or administering a second drug which mitigates said possible adverse events.

The present inventions further pertains to a S1P receptor modulator or agonist, e.g. FTY720, a phosphate derivative thereof or a pharmaceutically acceptable salt thereof, for use in a method for treating an inflammatory or an autoimmune disease or disorder, e.g. multiple sclerosis, wherein said method comprises the steps of
  i) monitoring the patient during a specific period of time after the first administration of said S1P receptor modulator or agonist, and
  N) optionally interrupting the administration of said S1P receptor modulator or agonist and/or modifying the treatment regimen thereof and/or administering a second drug which mitigates said possible adverse events.

In a specific embodiment, the present invention pertains to FTY720, a phosphate derivative thereof or a pharmaceutically acceptable salt thereof for use in a method for the treatment of multiple sclerosis, wherein said treatment comprises the steps of
  i) monitoring the patient during a specific period of time after the first administration of said S1P receptor modulator or agonist, and
  ii) optionally interrupting the administration of said S1P receptor modulator or agonist and/or modifying the treatment regimen thereof and/or administering a second drug which mitigates said possible adverse events.

According to the invention, the action taken on step ii) depends on the results obtained under step i).

When the S1P receptor modulator or agonist is selected from fingolimod (FTY720), a phosphate derivative thereof or a pharmaceutically acceptable salt thereof, the step of modifying the treatment regimen may consist of administering a daily dosage of the drug that is lower than about 0.5 mg and then increasing the dosage up to a daily dosage of about 0.5 mg. The dally dosage of the drug may then be increased stepwise, e.g. by titration. It may also consist of administering a daily dosage of the drug higher than 0.5 mg, e.g. a daily dosage of about 1.0 mg or about 1.25 mg.

In a specific embodiment of the invention, e.g. when the S1P receptor modulator or agonist is selected from fingolimod (FTY720), a phosphate derivative thereof or a pharmaceutically acceptable salt thereof, the step of modifying the treatment regimen may consist of increasing the period of time between two consecutive administrations of the medication.

According to the invention, there is provided a patient monitoring, i.e. a specific monitoring of patients treated with a S1P receptor modulator or agonist, such as fingolimod (FTY720), a phosphate derivative thereof or a pharmaceutically acceptable salt thereof, in order to control, limit or abolish the possible adverse events, wherein said monitoring is performed before and/or during administration of the medication.

The patient monitoring of the invention comprises
  a) monitoring infections or infestations, e.g. viral infections, throughout administering said S1P receptor modulator or agonist, and/or
  b) performing an ophthalmologic examination.

The patient monitoring may further comprise one or more steps of
  c) monitoring the heart rate of the patient at least during the first hours after the first administration of said S1P receptor modulator or agonist,
  d) observing the patient during the first hours after the first administration of said S1P receptor modulator or agonist, to monitor the heart rate of the patient,
  e) performing liver function tests,
  f) performing dermatological examinations,
  g) performing pulmonary functions tests.

The patient monitoring may further comprise one or more steps of
  h) determining complete blood counting (CBC),
  i) lymphocytes counting and/or recording of blood key parameters,
  j) monitoring and/or recording of vital signs, e.g. heart rate, blood pressure, e.g. arterial blood pressure.
  k) monitoring and/or recording of cardiac disorders,
  l) monitoring and/or recording of other adverse events or side-effects.

The invention also provides a dosing regimen and a method of controlling, reducing, or abolishing the possible adverse events associated with treating a patient suffering from an inflammatory or autoimmune disease or disorder with a S1P receptor modulator or agonist, comprising administering to said patient a therapeutically effective amount of said S1P receptor modulator or agonist, wherein said method comprises i) a patient monitoring as defined herein above, and
ii) optionally interrupting the administration of said S1P receptor modulator or agonist and/or modifying the treatment regimen thereof.

In one embodiment of the invention, the patient monitoring of the invention may comprise one or more of the following steps, optionally all the steps of,
  complete blood counting (CBC),
  lymphocytes counting,
  analysis of liver enzymes,
  monitoring and/or recording of vital signs, e.g. heart rate, blood pressure, e.g. arterial blood pressure,
  testing history of viral infection or viral serology, e.g. regarding chickenpox.
  monitoring and/or recording of infections or infestations, e.g. viral infections,
  dermatological examinations,
  ophthalmologic examinations,
  examinations of pulmonary function,
  monitoring and/or recording of cardiac disorders,
  monitoring and/or recording of blood key parameters,
  monitoring and/or recording of liver function tests,
  monitoring and/or recording of other adverse events or side-effects.

Preferably, the patient monitoring of the invention comprises one or more of the following steps, optionally all the steps of:
  complete blood counting (CBC),
  analysis of liver enzymes,
  ophthalmologic examinations, and
  testing history of viral infection or viral serology, e.g. regarding chickenpox,
  monitoring and/or recording of infections or infestations, e.g. viral infection.

The patient monitoring of the invention may further comprise
  establishing an electrocardiogram (ECG), e.g. at starting administration with the medication, and/or
  vaccinate the patient before starting administration, e.g. against varicella zoster virus (VZV).

As herein defined, the patient monitoring of the invention may comprise or more of the above described monitoring steps.

In one embodiment of the invention, the patient monitoring comprises the steps of
  monitoring and/or recording of infections or infestations, e.g. viral infections,
  performing ophthalmologic examinations, and optionally further comprises the steps of
  monitoring and/or recording of cardiac disorders for specific category of patients, and/or
  performing dermatological examinations.

In another embodiment of the invention, the patient monitoring comprises the steps of
  monitoring end/or recording of infections or infestations, e.g. viral infections,
  ophthalmologic examinations.
  monitoring and/or recording of cardiac disorders. e.g. for specific category of patients,
  liver function tests;

and optionally further comprises the steps of
dermatological examinations.

In yet a further embodiment of the invention, the patient monitoring comprises the steps of
monitoring the heart rate of the patient,
monitoring and/or recording of infections or infestations, e.g. viral infections,
performing ophthalmologic examinations,
and optionally further comprises the steps of
performing dermatological examinations.

In yet another embodiment of the invention, the patient monitoring comprises the steps of
monitoring and/or recording of infections or infestations, e.g. viral infections,
performing an ophthalmologic examination within the first 1 to 10 after starting administration,
observing patients for at least 6 hours after the first dose administration, and optionally further comprises the steps of
dermatological examinations.

The patient monitoring may further comprise a step of monitoring and/or recording of liver function tests in case patients develop symptoms suggestive of hepatic dysfunction.

In a preferred embodiment of the invention, there is provided a method of prescribing fingolimod (FTY720), a phosphate derivative thereof or a pharmaceutically acceptable salt thereof, to a patient in need thereof, in such a way as to limit the possible adverse events before of during administration of fingolimod, wherein said method comprises the patient monitoring as herein above described.

For example the method of prescribing fingolimod may comprise one or more of the following steps:
performing lymphocyte counting,
monitoring and/or recording of vital signs, e.g. blood pressure, e.g. arterial blood pressure,
monitoring and/or recording of infections or infestations, e.g. viral infections,
performing dermatological examinations,
performing ophthalmologic examinations,
performing examinations of pulmonary function,
monitoring and/or recording of cardiac disorders,
monitoring and/or recording of blood key parameters, e.g. level of serum ALT,
performing liver function tests,
monitoring and/or recording of other adverse events or side-effects, and
wherein each of said steps is performed for a specific period of time before and/or during the period of administering the drug.

The specific and regular monitoring of the treated patients may consist of one or more of the following steps
performing lymphocyte counting,
monitoring and/or recording of vital signs, e.g. blood pressure, e.g. arterial blood pressure,
monitoring and/or recording of infections or infestations, e.g. viral infections,
performing dermatological examinations,
performing ophthalmologic examinations,
performing examinations of pulmonary function,
monitoring and/or recording of cardiac disorders,
monitoring and/or recording of blood key parameters, e.g. level of serum ALT,
performing liver function tests,
monitoring and/or recording of other adverse events or side-effects, and
wherein said steps are performed for a specific period of time before and/or during the period of administering the drug.

Each step may be performed as further explained below.

Preferably, the patient monitoring may consist of one or more of the following steps:
monitoring and/or recording of infections or infestations, e.g. viral infections, during FTY720 therapy,
ophthalmologic examinations as herein defined,
monitoring and/or recording of cardiac disorders for specific category of patients,
liver function tests in case patients develop symptoms suggestive of hepatic dysfunction,
and optionally further comprises the steps of
dermatological examinations.

The different steps the patient monitoring of the invention are performed at a specific period of time after administration of the first dose.

These steps can be performed as described herein.

In a specific embodiment of the invention, the treated patients are monitored under supervision of medical doctors for a specific period of time after the first dose administration, for the first 1 to 10 hours after the first administration of the S1P receptor modulator or agonist, e.g. fingolimod, a phosphate derivative thereof or a pharmaceutically acceptable salt thereof, for at least 6 hours after the first dose administration.

According to the invention, one or more of these steps, e.g. monitoring and/or recording of cardiac disorders, are performed at least 4 hours after the first dose administration, e.g. at least for 6 hours after the first dose administration, or at least 8 hours alter the first dose administration, e.g. 3 to 8 hours after the first dose administration, e.g. 4 to 6 hours after the first dose administration, e.g. 4 to 6 hours after the first dose administration. Preferably monitoring and/or recording of cardiac disorders are performed about 6 hours after the first dose administration The step of monitoring and/or recording of cardiac disorders may consist of observing patients during that period of time after the first dose administration, e.g. during at least 4 hours after the first dose administration, e.g. at least for 6 hours after the first dose administration, or at least 8 hours after the first dose administration.

According to the invention, the cardiac disorders which are monitored and/or recorded comprise but are not limited to bradycardia and high-grade AV block.

According to the invention, the infections which are recorded or monitored are for example viral infections, e.g. varicella zoster virus (VZV), influenza viral infection, herpes viral infection, lower respiratory tract infection, e.g. bronchitis and pneumonia.

In an embodiment of the invention, the monitoring of infections or infestations is performed within the first three months after the first dose administration, e.g. within the first two months after the first dose administration. In another embodiment of the invention, the monitoring of infections or infestations is performed throughout administration of the medication.

Prior to starting administering the S1P receptor modulator or agonist, the patient may be tested for history of infections, e.g. viral infection, in particular chickenpox. In case the searched serology is negative, the patient may be vaccinated, e.g. against varicella zoster virus or influenza virus.

The monitoring or recording of infections or infestations, e.g. viral infections, may be performed with medical techniques available, for example through complete blood counting (CBC) and/or lymphocytes counting.

According to the invention, the ophthalmologic examination preferably comprises the checking and/or monitoring of disturbances in visual acuity, e.g. appearance of macular edema.

In a specific embodiment of the invention, eye examinations include at least one of eye history, visual acuity, dilated ophthalmoscopy, Optical Coherence Tomography (OCT), evaluation of the fundus. Such examinations are preferably performed by an ophthalmologist.

According to the invention, ophthalmologic examination may be performed after initiating the administration with S1P receptor modulator or agonist, e.g. after commencing FTY720 therapy, e.g. within the first 1 to 12 months, e.g. 2 to 10 months, e.g. 2 to 6 months, e.g. 2 to 5 months, e.g. 3 to 4 months. Additional ophthalmologic examinations may be performed as needed based on patient symptoms, e.g. at intervals determined by the ophthalmologist.

According to the invention, the ophthalmologic examination may comprising the steps of
1) identifying the eye diseases history of the patient to be treated before commencing the treatment with FTY720,
2) having ophthalmologic examinations performed as herein above mentioned, e.g. 3 to 4 months after commencing the treatment with FTY720, preferably by an ophthalmologist, and optionally
3) having additional ophthalmologic examinations performed based on patient symptoms, e.g. at intervals determined by the ophthalmologist.

Ophthalmologic examination may also be performed before starting the administration with S1P receptor modulator or agonist, e.g. before starting FTY720 therapy. This embodiment is particularly adapted for specific patients categories, for example in case of patients who have an eyes disease or disorder, and/or history of diabetes or uveitis.

According to the invention, the dermatological examination may comprise the checking of appearance e.g. of neoplasms, skin malignancies, melanoma, squamous cell carcinoma, basal cell carcinoma. Dermatological screening may be performed prior to, or shortly after initiation of therapy. In a specific embodiment of the invention, dermatological screenings are performed annually in patient receiving the S1P receptor modulator or agonist, e.g. FTY720, a phosphate derivative thereof or a pharmaceutically acceptable salt thereof.

Dermatological screening may be performed by a physician, e.g. a dermatologist. In another embodiments, such screening is performed more frequently, e.g. by the patient himself.

According to the invention, the examinations of pulmonary function may be performed by spirometry, pulmonary function tests, e.g. FEV1, FVC, FEF25-75%, DLCO, diffusion capacity for carbon monoxide, or chest high resolution computed tomography (HRCT).

In a specific embodiment of the invention the pulmonary function test (PFT) is performed a few hours to a few days after the first administration, for example at the day of the first administration, for example from 2 to 12 hours after the first drug administration, for example from 2 to 8 hours after the first drug administration, for example from 2 to 6 hours after the first administration, for example at 6-hour after the first administration. A second PFT may be performed a few days after the first administration, for example from 2 to 10 days after the first drug administration, for example from 3 to 8 days first drug administration, for example abut a week after the first drug administration.

In a specific embodiment of the invention the level of liver enzyme, e.g. serum ALT, is evaluated at initiation of therapy and optionally periodically thereafter. Continuous evaluation is particularly adapted in case of patients who develop symptoms suggestive of hepatic dysfunction.

According to the invention, the liver function tests may be performed for specific category of patients, e.g. patients who develop symptoms suggestive of hepatic dysfunction, e.g. nausea, vomiting, abdominal pain, anorexia, or jaundice.

According to the invention, monitoring and/or recording of liver function tests may comprise any one of the steps of
1) identifying the level of liver enzyme, e.g. serum ALT, in the patient to be treated before the first administration of the S1P receptor modulator or agonist, e.g. FTY720, a phosphate derivative thereof or a pharmaceutically acceptable salt thereof, and administering the first dose only if alanine aminotransferase (ALT) level is not more than 2 times the upper limit of the normal range (ULN),
2) identifying the level of liver enzyme, e.g. serum ALT, in the patient under therapy, and discontinue the therapy in patients experiencing jaundice or elevation of liver enzyme is more than 5 times the upper limit of the normal range (ULN).

The patient monitoring of the invention may comprise a step of observing the patient for the first 1 to 10 hours after the first administration of the S1P receptor modulator or agonist, e.g. fingolimod, a phosphate derivative thereof or a pharmaceutically acceptable salt thereof, e.g. the first 2 to 8 hours after the first administration, e.g. the first 3 to 9 hours after the first administration, e.g. the first 2 to 8 hours after the first administration, e.g. the first 4 to 7 hours after the first administration, e.g. the first 6 hours, e.g. the first 5 hours, e.g. the first 4 hours after the first administration of said S1P receptor modulator or agonist, e.g. fingolimod, a phosphate derivative thereof or a pharmaceutically acceptable salt thereof. For example, the patient monitoring of the invention may comprise a step of observing the patient at least 2 hours after the first administration of said S1P receptor modulator or agonist, e.g. fingolimod, a phosphate derivative thereof or a pharmaceutically acceptable salt thereof. e.g. at least 4 hours after the first administration, e.g. at least 6 hours after the first administration.

According to the present invention, there is provided a method for treating an inflammatory or autoimmune disease or disorder in a patient in need thereof, comprising administering to said patient a therapeutically effective amount of S1P receptor modulator or agonist, wherein specific parameters of the patient are checked before initiating said treatment, and if necessary, the treatment regimen is adapted and/or a second drug which mitigates the adverse events which could possibly occur.

The invention further pertains to a S1P receptor modulator or agonist, e.g. FTY720, a phosphate derivative thereof or a pharmaceutically acceptable salt thereof, for use in a method of treating an inflammatory or an autoimmune disease or disorder, e.g. multiple sclerosis, wherein said method comprises the steps of checking specific parameters of the patient before initiating said treatment, and if necessary adapting the treatment regimen thereof and/or administering a second drug which mitigates the adverse events which could possibly occur.

Said parameters are selected from signs of infections or infestations (e.g. viral infections), visual acuity, presence of eye disease, liver enzymes, blood pressure, blood analysis (e.g. complete blood count), electrocardiogram (ECG), pulmonary function, presence of skin disease or disorder, and liver function.

In a specific embodiment, these parameters are selected from signs of infections or infestations (e.g. viral infections), visual acuity, liver enzymes and blood pressure, and optionally heart rate.

For example, a ECG is performed before initiating administration with said S1P receptor modulator or agonist.

These parameters may also be checked throughout the treatment with said S1P receptor modulator or agonist.

In a specific embodiment of the invention there is provided

1—a method for administering a S1P receptor modulator or agonist, e.g. fingolimod, a phosphate derivative thereof or a pharmaceutically acceptable salt thereof, in a patient in need thereof, comprising the steps of
a.) identifying the eye diseases history of the patient to be treated before commencing the treatment with said S1P receptor modulator or agonist,
b.) having ophthalmologic examinations performed as herein above mentioned, e.g. 3 to 4 months after commencing the treatment with said S1P receptor modulator or agonist, preferably by an ophthalmologist, and optionally
c.) having additional ophthalmologic examinations performed based on patient symptoms, e.g. at intervals determined by the ophthalmologist.

2—A method for treating an inflammatory or autoimmune disease or disorder (for example multiple sclerosis), and limiting the symptoms associated thereof or reducing the severity of the disease, in a patient in need thereof, comprising the steps a.), b.) and c.) as defined above.

3—a S1P receptor modulator or agonist, e.g. FTY720, a phosphate derivative thereof or a pharmaceutically acceptable salt thereof, for use in a method for treating an inflammatory or an autoimmune disease or disorder, e.g. multiple sclerosis, wherein said method comprises the steps a.), b.) and c.) as defined above.

4—a S1P receptor modulator or agonist, e.g. FTY720, a phosphate derivative thereof or a pharmaceutically acceptable salt thereof, for use in the treatment of an inflammatory or an autoimmune disease or disorder, e.g. multiple sclerosis, wherein said treatment comprises the steps a.), b.) and c.) as defined above.

5—FTY720, a phosphate derivative thereof or a pharmaceutically acceptable salt thereof, e.g. the hydrochloride salt of FTY720, for use in a method for the treatment of multiple sclerosis, wherein said treatment comprises the steps of
a') identifying the eye diseases history of the patient to be treated before commencing the treatment with FTY720, phosphate derivative or pharmaceutically acceptable salt thereof,
a.) having ophthalmologic examinations performed as herein above mentioned, e.g. 3 to 4 months after commencing the treatment with FTY720, phosphate derivative or pharmaceutically acceptable salt thereof, preferably by an ophthalmologist, and optionally
b.) having additional ophthalmologic examinations performed based on patient symptoms, e.g. at intervals determined by the ophthalmologist.

6—FTY720, a phosphate derivative thereof or a pharmaceutically acceptable salt thereof, e.g. the hydrochloride salt of FTY720, for use in the treatment of multiple sclerosis, wherein said treatment comprises the steps a'.), b'.) and c'.) as defined above.

In a specific embodiment of the invention there is provided

7—A method for administering a S1P receptor modulator or agonist, e.g. fingolimod, a phosphate derivative thereof or a pharmaceutically acceptable salt thereof, in a patient in need thereof, comprising the steps of
d) identifying the level of liver enzyme, e.g. serum ALT, in the patient to be treated before the first administration of said S1P receptor modulator or agonist, and administering the first dose only if ALT level is not >2×ULN, and
e) identifying the level of liver enzyme, e.g. serum ALT, in the patient under therapy, and discontinue the therapy in patients experiencing jaundice or elevation of liver enzyme >5×ULN.

8—A method for treating an inflammatory or autoimmune disease or disorder (for example multiple sclerosis), and limiting the symptoms associated thereof or reducing the severity of the disease, in a patient in need thereof, comprising the steps d.), and e.) as defined above.

9—A S1P receptor modulator or agonist, e.g. FTY720, a phosphate derivative thereof or a pharmaceutically acceptable salt thereof, for use in a method for treating an inflammatory or an autoimmune disease or disorder, e.g. multiple sclerosis, wherein said method comprises the steps d.), and e.) as defined above.

10—A S1P receptor modulator or agonist, e.g. FTY720, a phosphate derivative thereof or a pharmaceutically acceptable salt thereof, for use in the treatment of an inflammatory or an autoimmune disease or disorder, e.g. multiple sclerosis, wherein said treatment comprises the steps d.), and e.) as defined above.

11—FTY720, a phosphate derivative thereof or a pharmaceutically acceptable salt thereof, e.g. the hydrochloride salt of FTY720, for use in a method for the treatment of multiple sclerosis, wherein said method comprises the steps of
d') identifying the level of liver enzyme, e.g. serum ALT, in the patient to be treated before the first administration of FTY720, a phosphate derivative thereof or a pharmaceutically acceptable salt thereof, and administering the first dose only if ALT level is not >2×ULN, and
e') identifying the level of liver enzyme, e.g. serum ALT, in the patient under therapy, and discontinue the therapy in patients experiencing jaundice or elevation of liver enzyme >5×ULN 12—FTY720, a phosphate derivative thereof or a pharmaceutically acceptable salt thereof, e.g. the hydrochloride salt of FTY720, for use in the treatment of multiple sclerosis, wherein said treatment comprises the steps d'.), and e'.) as defined above.

In yet another embodiment of the invention there is provided

13—A method for administering a S1P receptor modulator or agonist, e.g. FTY720, a phosphate derivative thereof or a pharmaceutically acceptable salt thereof, in a patient in need thereof and receiving concomitant beta-blocker therapy, comprising the steps of
f) measuring heart rate and/or blood pressure of the patient to be treated before commencing the treatment with said S1P receptor modulator or agonist,
g) either measuring heart rate every 3 to 5 hour, e.g. every four hour, for at least 6 hour hereafter, and/or perform an ECG 3 to 6 hours, e.g. 4 to 6 hours, post-dose, and
h) administering an adequate treatment if bradyarrhythmia-related symptom is seen under step g), e.g. atropine or isoprenaline.

In one embodiment, that method refers to a method for administering FTY720, a phosphate derivative thereof or a pharmaceutically acceptable salt thereof, e.g. the hydrochloride salt of FTY720, in a patient affected by multiple sclerosis.

14—A method for treating an inflammatory or autoimmune disease or disorder (for example multiple sclerosis), and limiting the symptoms associated thereof or reducing the severity of the disease, in a patient in need thereof, comprising the steps f.), g.) and h.) as defined above.

15—A S1P receptor modulator or agonist, e.g. FTY720, a phosphate derivative thereof or a pharmaceutically acceptable salt thereof, for use in a method for treating an inflammatory or an autoimmune disease or disorder, e.g. multiple sclerosis, wherein said method comprises the steps f.), g.) and h.) as defined above.

16—A S1P receptor modulator or agonist, e.g. FTY720, a phosphate derivative thereof or a pharmaceutically acceptable salt thereof, for use in the treatment of an inflammatory or an autoimmune disease or disorder, e.g. multiple sclerosis, wherein said treatment comprises the steps f.), g.) and h.) as defined above.

17—FTY720, a phosphate derivative thereof or a pharmaceutically acceptable salt thereof, e.g. the hydrochloride salt of FTY720, for use in a method for the treatment of multiple sclerosis, wherein said method comprises the steps of f') measuring heart rate and/or blood pressure of the patient to be treated before commencing the treatment with FTY720, a phosphate derivative thereof or a pharmaceutically acceptable salt thereof, g') either measuring heart rate every 3 to 5 hour, e.g. every four hour, for at least 6 hour hereafter, and/or perform an ECG 3 to 6 hours, e.g. 4 to 8 hours, post-dose, and h') administering an adequate treatment if bradyarrhythmia-related symptom is seen under step g), e.g. atropine or isoprenaline.

18—FTY720, a phosphate derivative thereof or a pharmaceutically acceptable salt thereof, e.g. the hydrochloride salt of FTY720, for use in the treatment of multiple sclerosis, wherein said treatment comprises the steps of f.), g'.) and h'.) as defined above.

In yet another embodiment of the invention there is provided

19—A method for administering a S1P receptor modulator or agonist, e.g. FTY720, a phosphate derivative thereof or a pharmaceutically acceptable salt thereof, in a patient in need thereof, comprising the steps of i) observing the patient after the first dose administration for an observing period as defined hereinabove, e.g. for at least 6 hours j) measuring heart rate of the patient after this period, k) either releasing the patient if the if the is >40 bpm, or of 40-60 bpm e.g. in case this value is not the lowest heart rate measured during the 6-hour observation period; or maintaining the patient in an appropriate setting.

Such a method is particularly adapted to patients with low resting heart rate (e.g. lower than 50) or those taking beta blockers, or having high grade atrio-ventricular (AV) block or sick-sinus syndrome.

In a specific embodiment, that method refers to a method for administering FTY720, a phosphate derivative thereof or a pharmaceutically acceptable salt thereof, e.g. the hydrochloride salt of FTY720, in a patient affected by multiple sclerosis.

The present invention also provides

20—FTY720, a phosphate derivative thereof or a pharmaceutically acceptable salt thereof, e.g. the hydrochloride salt of FTY720, for use in the treatment of multiple sclerosis, wherein said treatment comprises the steps i.), j.) and k.) as defined above.

21—FTY720, a phosphate derivative thereof or a pharmaceutically acceptable salt thereof, e.g. the hydrochloride salt of FTY720, for use in a method of treating multiple sclerosis, wherein said method comprises the steps i.), j.) and k.) as defined above.

In specific cases, e.g. when patients experiencing symptomatic events associated with braddyarrythmia not resolved by the end of the 6 hour observation, day 2 dose may also be performed with an observation period like the first administration, e.g. as described above.

An observation period as defined hereinabove, e.g. 6 hour observation, may also be performed in case of a patient restarting the S1P receptor modulator or agonist, e.g. FTY720, a phosphate derivative thereof or a pharmaceutically acceptable salt thereof, after a drug interruption of more than 4 days, e.g. more than 6 days, e.g. more than 8 days, e.g. more than 10 days, e.g. more than 12 days, e.g. more than 14 days, e.g. more than 18 days, e.g. more than 21 days.

In another embodiment of the invention, there is provided a method for administering FTY720, a phosphate derivative thereof or a pharmaceutically acceptable salt thereof, to a patient in need thereof while controlling, limiting or abolishing the possible adverse events associated or in relation to such an administering, wherein the patients at possible risk of showing such events are identified before administering the drug and specific and regular monitoring of the treated patients is performed, e.g. by an adequate physician.

The patients at possibly increased risk may be patients selected from patients who have eyes diseases or disorders; patients who show a high ALT level, patients who have hepatic dysfunction, patients who have hypertension; and patients who have heart failure or arrythmias. It may also concern patient affected by asthma, for example moderate asthma and/or diabetic patients.

In another embodiment, it can be pregnant women.

As herein defined, an eyes disease or disorder refers to a disease or disorder impacting eyes, e.g. uveitis, diabetes.

Patients who show a high ALT level refers to patients who show an ALT level of, or superior to, 2 times than ULN, e.g. before initiating FTY720 treatment)

Patients who have heart disorders refers to one or more disorders selected from high-grade AV block, sick sinus syndrome, ischeamic heart disease, congestive heart failure, and arrhythmia. For example, this concerns patients suffering from or at risk of bradyarrhythmia, patients with high grade atrio-ventricular blocks or sick sinus syndrome, patients with a history of syncopal episodes, or patients under beta blockers or anti-arrhythmic treatment, such as patients under anti-arrhythmic drugs.

According to the invention, there is provided a specific monitoring of patients treated with a S1P receptor modulator or agonist, e.g. FTY720, a phosphate derivative thereof or a pharmaceutically acceptable salt thereof, wherein said patients are suffering from an inflammatory or an autoimmune disease or disorder. e.g. multiple sclerosis, comprising any ones of the following steps of:

i) observation period, e.g. at least 6 hour, e.g. 4 to 6 hours, during which or at the end of which heart rate is checked, as defined herein, ii) annual skin examination after first dose administration, as defined herein, iii) regular review of liver enzyme, e.g. serum ALT, as defined herein,
iv) ophthalmologic examinations 2 to 12 months, e.g. 3 to 4 months, after first dose administration, as defined herein,
v) regular checking of patient visual function, as defined herein.

There is further provided method of administering a S1P receptor modulator or agonist, e.g. fingolimod in the form of FTY720, a phosphate derivative thereof or a pharmaceutically acceptable salt thereof, to patients suffering from an inflammatory or an autoimmune disease or disorder, e.g. multiple sclerosis, comprising
a) performing any ones of the following steps of:
i) observation period, e.g. at least 6 hour, e.g. 4 to 6 hours, during which or at the end of which heart rate is checked, as defined herein,
ii) annual skin examination after first dose administration, as defined herein,
iii) regular review of liver enzyme, e.g. serum ALT, as defined herein,
iv) ophthalmologic examinations 3 to 4 months after first dose administration, as defined herein,
v) regular checking of patient visual function, as defined herein;
and
b) if required, interrupting fingolimod administration based upon the results of one of more of the above steps or changing the treatment regimen and/or administering a second drug. Step b) may correspond to appearance of adverse events. The second drug may be a drug which mitigates said possible adverse events.

Interrupting fingolimod administration, changing the treatment regimen and/or administering a second drug, may occur in case of any of the following conditions: bradycardia or atrioventricular conduction abnormalities, macular edema or other visual disturbance, skin cancer, altered liver functions or liver injury, infections or hypertension. Duration of the interruption is defined by the physician.

Interrupting fingolimod administration, changing the treatment regimen and/or administering a second drug, may also occur in case the lymphocyte count of the patient becomes abnormally low, or becomes lower than 2001 mL.

For example, step a) may comprise one or more steps of
i) monitoring the heart rate of the patient,
ii) monitoring infections or infestations, e.g. viral infections, and
iii) performing ophthalmologic examination within the first 1 to 10 after starting administration.

Therapeutic Dosages

In a preferred embodiment of the invention the methods for administering FTY720, a phosphate derivative thereof or a pharmaceutically acceptable salt thereof as defined herein above, in particular the methods for treating an inflammatory or autoimmune disease or disorder, limiting the symptoms associated thereof or the progression thereof, e.g. multiple sclerosis, in a patient in need thereof comprise administering a daily dosage of FTY720, a phosphate derivative thereof or a pharmaceutically acceptable salt thereof, e.g. FTY720 hydrochloride, of not more than 0.5 mg, e.g. of about 0.5 mg.

According to the invention there is provided a compound selected from fingolimod (FTY720), a phosphate derivative thereof or a pharmaceutically acceptable salt thereof, e.g. fingolimod hydrochloride, for use in treating or preventing an inflammatory or autoimmune disease, whereby said compound is administered in such a way to a patient that the adverse events possibly associated with administration of said compound are controlled, limited, reduced or abolished. For example, the daily dosage of fingolimod (FTY720), a phosphate derivative thereof or a pharmaceutically acceptable salt thereof, e.g. fingolimod hydrocholoride, does not exceed 0.5 mg, e.g. is of about 0.5 mg.

In a specific embodiment of the invention there is provided a method for treating multiple sclerosis, controlling or limiting the symptoms associated thereof or reducing the severity of said disease in a patient in need thereof, comprising administering a daily dosage of fingolimod (FTY720), a phosphate derivative thereof or a pharmaceutically acceptable salt thereof, e.g. fingolimod hydrocholoride, wherein said daily dosage does not exceed 0.5 mg, e.g. is of about 0.5 mg, and wherein the patient is further affected by asthma (for example moderate asthma), by a disease or disorder impacting eyes or has an history of eyes diseases or disorders (for example is affected by uveitis or diabetes), show high-grade AV block, sick sinus syndrome, hepatic dysfunction or hypertension.

In a further embodiment of the invention there is provided a method for treating multiple sclerosis, controlling or limiting the symptoms associated thereof or reducing the severity of said disease in a patient in need thereof, comprising administering a daily dosage of fingolimod (FTY720), a phosphate derivative thereof or a pharmaceutically acceptable salt thereof, e.g. fingolimod hydrocholoride, wherein said daily dosage does not exceed 0.5 mg, e.g. Is of about 0.5 mg, and wherein the patient is pregnant.

In yet a further embodiment of the invention there is provided a method for treating multiple sclerosis, limiting the symptoms associated thereof or reducing the severity of said disease in a patient in need thereof, comprising administering a daily dosage of fingolimod (FTY720), a phosphate derivative thereof or a pharmaceutically acceptable salt thereof, e.g. fingolimod hydrocholoride, wherein said daily dosage does not exceed 0.5 mg, e.g. is of about 0.5 mg, and wherein the patient is a MS patients who has never received treatment for MS, e.g. do novo patient.

According to the invention, adopting the treatment regimen may consist of decreasing the dosage, or increasing the time between two consecutive administrations of the S1P receptor modulator or agonist, e.g. fingolimod, a phosphate derivative thereof or a pharmaceutically acceptable salt thereof. For example it may consist of administering 0.25 mg of fingolimod, a phosphate derivative thereof or a pharmaceutically acceptable salt thereof, two times a day. It may also consist of increasing stepwise the dosage of the drug during the first period of administration up to a daily dosage of 0.5 mg or 1.25 mg, e.g. adopting a stepwise administration, e.g. a titration.

The present invention pertains to a method for treating multiple sclerosis comprising
(a) administering a varied dose of a drug selected from the group consisting of fingolimod (FTY720), a phosphate derivative thereof or a pharmaceutically acceptable salt thereof in a patient in need thereof,
(b) monitoring adverse events occurring in said patient,
(c) monitoring reduction or abolition of symptoms associated with multiple sclerosis, and
(d) determining optimal dose for said patient The daily dose of the drug may be not exceeding 0.5 mg.
In another embodiment, the daily dose of the drug is above 0.5 mg, e.g. is about 1.00 mg, e.g. about 1.25 mg, e.g. about 1.5 mg.

There is also provided a S1P receptor modulator or agonist, e.g. FTY720, a phosphate derivative thereof or a pharmaceutically acceptable salt thereof, for use in a method for treating an inflammatory or autoimmune disease, e.g. multiple sclerosis, wherein said method comprises
(a) administering a varied dose of said S1P receptor modulator or agonist in a patient in need thereof,
(b) monitoring adverse events occurring in said patient,
(c) monitoring reduction or abolition of symptoms associated with said inflammatory or autoimmune disease, and
(d) determining optimal dose for said patient.

This method is particularly adapted for FTY720, a phosphate derivative thereof or a pharmaceutically acceptable salt thereof, e.g. FTY720 hydrochloride, for treating multiple sclerosis.

When the S1P receptor modulator or agonist is selected from FTY720, a phosphate derivative thereof or a pharmaceutically acceptable salt thereof, e.g. is FTY720 hydrochloride, and the disease is multiple sclerosis, the daily dose of the drug may not be exceeding 0.5 mg.

In another embodiment, the S1P receptor modulator or agonist is selected from FTY720, a phosphate derivative thereof or a pharmaceutically acceptable salt thereof, e.g. FTY720 hydrochloride, and the daily dose is exceeding 0.5 mg, e.g. is about 1.00 mg, e.g. about 1.25 mg, e.g. about 1.5 mg.

In yet a further embodiment of the invention, there is provided a personalized method for treating an inflammatory or autoimmune disease or disorder, e.g. multiple sclerosis, in a patient in need thereof comprising administering to said patient a therapeutically effective amount of a S1P receptor modulator or agonist,
wherein said method comprises
(a) administering a varied dose of said drug to the patient,
(b) monitoring adverse events occurring in said patient,
(c) monitoring reduction or abolition of symptoms associated with multiple sclerosis, and
(d) determining optimal dose for said patient,
wherein said regimen is adapted for treating said disease or disorder and controlling, reducing, or abolishing the possible adverse events associated with administering said S1P receptor modulator or agonist.

The steps (a) to (d) above may also be used in a method for determining a personalized therapeutic treatment regimen of a drug selected from the group consisting of fingolimod (FTY720), a phosphate derivative thereof or a pharmaceutically acceptable salt thereof, in a patient suffering from an inflammatory or autoimmune disease, e.g. multiple sclerosis.

The present invention also pertains a compound selected from FTY720, a phosphate derivative thereof or a pharmaceutically acceptable salt thereof, e.g. FTY720 hydrochloride, for use in a method for treating an inflammatory or autoimmune disease or disorder in a patient in need thereof, wherein said method is personalized, e.g. is adapted for treating said disease or disorder to the specific profile of the patient in such a way that the adverse events associated with administering said S1P receptor modulator or agonist are controlled, reduced, or abolished. In such a case, the patient to be treated my be selected from patients who have never received treatment for that disease or disorder, patients suffering or at risk of heart failure or arrythmias, patients affected by asthma, patients who have eyes diseases or disorders, hepatic dysfunction or hypertension.

The present invention provides for a compound selected from FTY720, a phosphate derivative thereof or a pharmaceutically acceptable salt thereof, e.g. FTY720 hydrochloride, for use in treating patients suffering from an inflammatory or an autoimmune disease or disorder, e.g. multiple sclerosis, wherein the compound is administered through the administration pattern defined above.

The present invention also provides for a compound selected from FTY720, a phosphate derivative thereof or a pharmaceutically acceptable salt thereof, e.g. FTY720 hydrochloride, for use in treating patients suffering from an inflammatory or an or disorder disease, e.g. multiple sclerosis, wherein the compound is administered through the patient monitoring defined above.

Combination

In another embodiment of the invention, the S1P receptor modulator, e.g. fingolimod (FTY720), a phosphate derivative thereof or a pharmaceutically acceptable salt thereof, e.g. fingolimod hydrochloride, is administered together with a second drug which mitigates the possible adverse event associated with administration of fingolimod.

Such a second drug may be administered only in the event that an adverse event, e.g. a side-effect, occurs or increases in intensity or frequency to a level which is not acceptable anymore, e.g. as hereinabove described.

The second drug may be selected from the group consisting of drugs which treat or prevent macular edema, anti-cancer agents (e.g. chemotherapeutic agents), anti-infection agents, anti-hypertensive drugs, anti-bradychardia agents, and mixture thereof.

Examples of second drug include, but are not limited to, calcium channel blocker (e.g. diltiazem), atenolol, valsartan, When the S1P receptor modulator or agonist of the invention, e.g. fingolimod (FTY720), a phosphate derivative thereof or a pharmaceutically acceptable salt thereof, e.g. fingolimod hydrochloride, is administered together with a second drug which mitigates the possible adverse event associated with administration of fingolimod, the daily dosage of said S1P receptor modulator or agonist may be above 0.5 mg, e.g. may be about 1.00 mg, e.g. about 1.25 mg, e.g. about 1.5 mg.

For example there is provided a combination, e.g. a kit, containing a S1P receptor modulator or agonist of the invention, e.g. fingolimod (FTY720), a phosphate derivative thereof or a pharmaceutically acceptable salt thereof, e.g. fingolimod hydrocholoride, and a second drug which is selected from the group consisting of anti-cancer agents, anti-infection agents, anti-microbial agents, anti-viral therapy, and anti-hypertensive drugs, whereby the dosage of said S1P receptor modulator or agonist is above 0.5 mg, e.g. is about 1.25 mg.

The invention also provides a specific dosage regimen of FTY720 for treating an inflammatory or autoimmune disease or disorder, limiting the symptoms associated thereof or the progression thereof, e.g. multiple sclerosis, in a patient in need thereof, comprising administering to said patient a daily dosage of fingolimod (FTY720), a phosphate derivative thereof or a pharmaceutically acceptable salt thereof, which leads to a reduction of peripheral lymphocyte count of about 70 to 75%, e.g. of about 73%, 75% or 76%.

In another embodiment the invention provides a specific dosage regimen of FTY720 for treating an inflammatory or autoimmune disease or disorder, limiting the symptoms associated thereof or the progression thereof, e.g. multiple sclerosis, in a patient in need thereof, comprising administering to said patient a daily dosage of fingolimod (FTY720), a phosphate derivative thereof or a pharmaceutically acceptable salt thereof, which leads to a reduction of peripheral lymphocyte count to a level low enough to obtain the therapeutic effect on the disease while controlling, limiting or abolishing the incidence of infections. Preferably this daily dosage is not more than 0.5 mg of fingolimod (FTY720), a phosphate derivative thereof or a pharmaceutically acceptable salt thereof, e.g. of the hydrochloride salt thereof Utility of the dosage regimen of the invention in treating diseases and conditions as hereinabove specified may be demonstrated in standard animal or clinical tests, e.g. in accordance with the methods described hereinafter.

Example 1

Study:

Two different daily dosages of fingolimod (0.5 mg and 1.25 mg) have been orally administered to patients with Relapsing-remitting Multiple Sclerosis during 24-month 1292 patients with RRMS from 172 centers in 18 countries are randomized to receive oral fingolimod, in a dose of 0.5 mg/day or 1.25 mg/day, or interferon beta1-a 30 µg intramuscularly once a week. Patients randomized to fingolimod receive placebo injections once a week, and those randomized to interferon beta1-a receive a placebo pill once a day.

The patients are seen clinically every month for 3 months and every 3 months thereafter. The Expanded Disability Status Scale (EDSS) is performed every 3 months, the MS Functional Composite (MSFC) every 6 months, and MRI annually. Monitoring by ophthalmic examination, dermatologic examination, pulmonary function tests, chest X-ray and/or CT, Holter monitoring, and echocardiography are performed.

Participants who completed 1 year on treatment are offered an optional extension phase. Those randomized to fingolimod continue on their assigned dose, and those in the interferon beta1-a group are randomized to the 2 fingolimod doses.

Results:

There are reduced relapses in both fingolimod groups compared with interferon beta1-a. For the lower dose, there is a 52% reduction in relapses vs interferon beta1-a, and a 38% reduction with the higher dose. Results in both fingolimod groups are highly statistically significant vs interferon beta1-a, but not statistically different from each other.

| End Point | Interferon beta1-a | Fingolimod 0.5 mg/day | P | Fingolimod 1.25 mg/day | P |
|---|---|---|---|---|---|
| Annualized relapse rate | 0.33 | 0.16 | <.0001 | 0.20 | <.0001 |

The proportion of relapse-free patients is 83% with fingolimod vs 69% in the interferon beta1-a group.

MRI lesion activity shows a reduction in both fingolimod groups in the number of new or newly enlarging T2 lesions and the number of gadolinium-enhancing T1 lesions at month 12.

Observed adverse events include bradycardia and atrioventricular (AV) block, and infections, including 3 herpes viral infections.

| Type | Interferon beta1-a, n (%) | Fingolimod 0.5 mg/d, n (%) | Fingolimod 1.25 mg/day, n (%) |
|---|---|---|---|
| Basal-cell carcinoma | 1 (0.2) | 3 (0.7) | 2 (0.5) |
| Squamous-cell carcinoma | 1 (0.2) | 0 | 0 |
| Malignant melanoma | 0 | 3 (0.7) | 0 |
| Breast cancer | 0 | 2 (0.5) | 2 (0.5) |

Example 2

Study:

Patients with moderate asthma are divided into 3 dosing cohorts of 12 patients each. In each cohort, the 12 patients are randomized to FTY720 (0.5 mg, 1.25 mg, and 2.5 mg in cohorts 1, 2, and 3 respectively) or placebo in a 3:1 ratio resulting in 9 patients treated with FTY720 at each dose level and 9 patients treated with placebo.

The study consists of a screening period of between 12 and 26 days, baseline and a 10 day treatment period followed by a study completion evaluation (performed 1-7 days after the last dose).

Two screening visits are performed, the initial Screening visit and a second visit at Day −7 (+/−1 day). The initial screening visit (Visit 1) is used to start pulmonary function test (PFT) monitoring to assess eligibility for the study and to obtain relevant background information and informed consent. The PFT is performed at a clock time similar to the 6-hour post-dose timepoint on Day 1. On Day −7 a PFT is again performed at the specified time. Short-acting β2 agonist use prior to treatment with study medication is also recorded in this 14 day period.

Patients return to the clinic one or 2 days prior to dosing for baseline assessments. PFT profiling is assessed at 7 time points during the visit and routine baseline evaluations are performed. On Day 1, patients are randomized in a 3:1 ratio to FTY720 or placebo and PFT profiling is assessed at 8 time points (namely pro-dose, then at 1, 2, 3, 4, 5, 6 and 12 hours post-dose). PFT assessments are also performed on Days 2, 3, 7 (all single time points assessed at approximately the same dock time as the 6 hours post-dose PFT on Day 1) and Day 10 (7 time points, namely pre-dose and then at 1, 2, 3, 4, 5 and 6 hours post-dose). On each of the days when PFT assessments are performed, a reversibility test follows the last PFT assessment of the day. Short-acting β2 agonist use is also recorded throughout the treatment period up to and including Day 11 (24 hours post last dose).

Blood samples are collected on Day 1 at pre-dose and at 1, 2, 4, 6, 8, 12, 16, and 24 h postdose, on Days 2, 3 and 7 at 6 hours post-dose and on Day 10 at predose and at 1, 2, 4, and 6 h post-dose.

Safety assessments include physical examinations, ECGs, vital signs, spirometry assessments, standard clinical laboratory evaluations (hematology, blood chemistry, urinalysis), adverse event and serious adverse event monitoring.

Only one half of each treatment cohort, a maximum of 6 patients, is allowed to start treatment on any given day for safety reasons. At least 1 day (24 hours) separates the initial dosing of the first group of patients from the dosing of the second group (and at least 1 further day separates the second group from any subsequent groups required to complete each cohort).

The magnitude and time course of the effect of FTY720 on FEV1 and other pulmonary function tests (FVC, FEF25-75%, and FEV1/FVC) is measured.

Results:

The magnitude of the bronchoconstriction is primarily assessed by the baseline-adjusted $FEV_1$ AUC0-6 h on Day 1. This primary PD variable is defined as the ratio of the AUEC $FEV_1$ over the 6-hour PFT profile on Day 1 divided by the same variable at baseline (Day −1).

This primary PD variable is analyzed on the log-scale by means of a linear model adjusted for the (log-transformed) baseline $FEV_1$ AUC0-6 h and the treatment group as fixed effects. The geometric mean baseline-adjusted $FEV_1$ AUC0-6 h is obtained from the model for each treatment group; the geometric mean ratio between each FTY720 group and placebo is also obtained along with its 95% Cl, and is back-transformed to obtain the geometric mean percent change from placebo and its 95% Cl.

Additional PD variables are calculated: baseline-adjusted $FEV_1$ AUC0-6 h on Day 10 and baseline-adjusted $FEV_1$ Emax1-6 h on Days 1 and 10. The Emax variables are defined as the ratio between Day 1 (or Day 10) and Day −1 regarding the minimum from 6 assessments scheduled at 1 to 6 hours post dose. Those variables are defined for $FEV_1$ as well as for the other PFT parameters (FVC, $FEF_{25-75\%}$, and $FEV_1/FVC$) and are analyzed using the same model as for the primary PD endpoint.

The time-course of the PFT parameters is explored on Day 1 over the 12-hour profile and on Day 10 over the 6-hour profile. The percent change from time-matched baseline in $FEV_1$, FVC, $FEF_{25-75\%}$, and $FEV_1/FVC$ is summarized by means of descriptive statistics at each visit/time point. The log-transformed ratio from time-match baseline is analyzed, separately at each post-baseline visit/time point, by means of a linear model adjusted for the time-matched log-transformed baseline value and the treatment group as fixed effect. For each FTY720 group, the estimate for the mean treatment difference versus placebo and its 95% Cl are obtained from the model and are back-transformed to obtain the geometric mean percent change from placebo and its 95% Cl. No adjustment was made to the P values for multiple testing.

The results show that at a daily dosage of 0.5 mg FTY720 is safe and well tolerated in patients with moderate asthma.

The invention claimed is:

1. A method for treating relapsing remitting multiple sclerosis in a patient in need thereof, the method comprising:
   (a) identifying a patient at risk of contracting infection caused by varicella zoster virus by testing said patient for a history of infection caused by varicella zoster virus,
   (b) vaccinating the patient at risk of contracting infection caused by varicella zoster virus, and
   (c) administering orally fingolimod or a pharmaceutically acceptable salt thereof to said patient at a daily dosage of 0.5 mg,
   thereby limiting the risk of infection caused by varicella zoster virus.

2. The method according to claim 1, wherein treating comprises reducing the frequency of clinical exacerbations.

3. The method according to claim 1, wherein fingolimod is administered as a hydrochloride salt.

4. The method according to claim 1, wherein the infection is chickenpox.

* * * * *

Disclaimer

10,543,179 B2 — Craig Boulton, Horsham (GB); Pascale Burtin, Huningue (FR); Oliver David, Mulhouse (FR); Ana de Vera, Basel (CH); Thomas Dumortier, Basel (CH); Irene Hunt, Basel (CH); Robert Schmouder, Berkeley Heights, NJ (US); William C. Collins, Basel (CH). DOSAGE REGIMEN OF AN S1P RECEPTOR MODULATOR. Patent dated January 28, 2020. Disclaimer filed January 24, 2020, by the assignee, Novartis Pharmaceuticals Corporation.

Hereby disclaims the term of this patent which would extend beyond December 25, 2027.

*(Official Gazette, March 3, 2020)*